United States Patent
Wozencroft

(10) Patent No.: US 9,440,026 B2
(45) Date of Patent: *Sep. 13, 2016

(54) AUTOINJECTION DEVICES

(71) Applicant: OWEN MUMFORD LIMITED, Oxford (GB)

(72) Inventor: Robert Michael Wozencroft, Surrey (GB)

(73) Assignee: OWEN MUMFORD LIMITED, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/578,951

(22) Filed: Dec. 22, 2014

(65) Prior Publication Data

US 2015/0112262 A1 Apr. 23, 2015

Related U.S. Application Data

(63) Continuation of application No. 13/058,238, filed as application No. PCT/GB2009/051016 on Aug. 13, 2009, now Pat. No. 8,932,266.

(60) Provisional application No. 61/095,477, filed on Sep. 9, 2008.

(30) Foreign Application Priority Data

Aug. 13, 2008 (GB) .................................. 0814747.2

(51) Int. Cl.
*A61M 5/32* (2006.01)
*A61M 5/20* (2006.01)
(Continued)

(52) U.S. Cl.
CPC ......... *A61M 5/2033* (2013.01); *A61M 5/3257* (2013.01); *A61M 5/50* (2013.01); *A61M 5/24* (2013.01); *A61M 5/326* (2013.01); *A61M 5/425* (2013.01); *A61M 5/46* (2013.01);
(Continued)

(58) Field of Classification Search
CPC ........... A61M 5/3257; A61M 5/2033; A61M 5/326; A61M 2005/2414; A61M 2005/2073; A61M 2005/2013; A61M 2005/3261; A61M 2005/206; A61M 2005/2407; A61M 5/50; A61M 2005/1402; A61M 2005/2411; A61M 5/3146; A61M 5/46; A61M 5/425; A61M 5/24

See application file for complete search history.

(56) References Cited

U.S. PATENT DOCUMENTS 2,660,169 A * 11/1953 Malm .................. A61M 5/32
604/115
3,880,163 A * 4/1975 Ritterskamp ............... 604/136
(Continued)

FOREIGN PATENT DOCUMENTS

DE  102005038933  2/2007
EP  0666084  8/1995
(Continued)

*Primary Examiner* — Bhisma Mehta
*Assistant Examiner* — Jenna Zhang
(74) *Attorney, Agent, or Firm* — Young & Thompson

(57) ABSTRACT

An autoinjection device includes a main body in the front end of which is slideably mounted a drawer or front body portion. The drawer can be opened to remove or insert a syringe. Closing the drawer while pressing a multifunction button primes the drive mechanism by latching it against trigger latch. Pressing the button gain while urging the front end causes the drawer to release the trigger latch. After the injection the drawer shrouds the used needle and can be released only by pressing the button.

26 Claims, 12 Drawing Sheets

(51) Int. Cl.
*A61M 5/50* (2006.01)
*A61M 5/24* (2006.01)
*A61M 5/46* (2006.01)
*A61M 5/42* (2006.01)

(52) U.S. Cl.
CPC *A61M2005/206* (2013.01); *A61M 2005/2013* (2013.01); *A61M 2005/2073* (2013.01); *A61M 2005/2414* (2013.01)

(56) References Cited

U.S. PATENT DOCUMENTS

| | | | | |
|---|---|---|---|---|
| 5,267,963 | A | | 12/1993 | Bachynsky |
| 5,271,744 | A | * | 12/1993 | Kramer ............... A61M 5/1723 604/135 |
| 5,320,609 | A | | 6/1994 | Haber et al. |
| 5,342,309 | A | * | 8/1994 | Hausser ............... A61M 5/3243 604/110 |
| 5,478,316 | A | * | 12/1995 | Bitdinger ............ A61M 5/2033 604/134 |
| 6,099,503 | A | * | 8/2000 | Stradella ............ A61M 5/2033 604/131 |
| 6,123,684 | A | | 9/2000 | Deboer et al. |
| 6,270,479 | B1 | * | 8/2001 | Bergens ............... A61M 5/2033 604/156 |
| 6,706,049 | B2 | * | 3/2004 | Moerman ............ A61B 5/1411 604/164.06 |
| 2005/0033234 | A1 | * | 2/2005 | Sadowski ........... A61M 5/2033 604/140 |
| 2006/0184189 | A1 | * | 8/2006 | Olson .................. A61B 5/1411 606/181 |
| 2006/0264830 | A1 | | 11/2006 | Hommann |
| 2009/0118752 | A1 | * | 5/2009 | Perez .................. A61B 5/1411 606/181 |
| 2009/0259181 | A1 | | 10/2009 | Moser |
| 2010/0010374 | A1 | * | 1/2010 | Escutia ................ A61B 5/1411 600/576 |
| 2010/0191184 | A1 | * | 7/2010 | Choi ...................... A61M 5/46 604/117 |
| 2011/0166509 | A1 | * | 7/2011 | Gross .................... A61M 5/425 604/60 |
| 2011/0172602 | A1 | * | 7/2011 | Eaton ................. A61M 5/2033 604/134 |

FOREIGN PATENT DOCUMENTS

| | | |
|---|---|---|
| GB | 728248 | 4/1955 |
| GB | 891887 | 3/1962 |
| JP | H06233820 | 8/1994 |
| JP | H07222799 | 8/1995 |
| JP | H11503637 | 3/1999 |
| JP | 2006506185 | 2/2006 |
| JP | 2007509657 | 4/2007 |
| WO | 03068290 | 8/2003 |
| WO | 2004045375 | 6/2004 |
| WO | 2004098687 | 11/2004 |
| WO | 2007066152 | 6/2007 |
| WO | 2007115424 | 10/2007 |

* cited by examiner

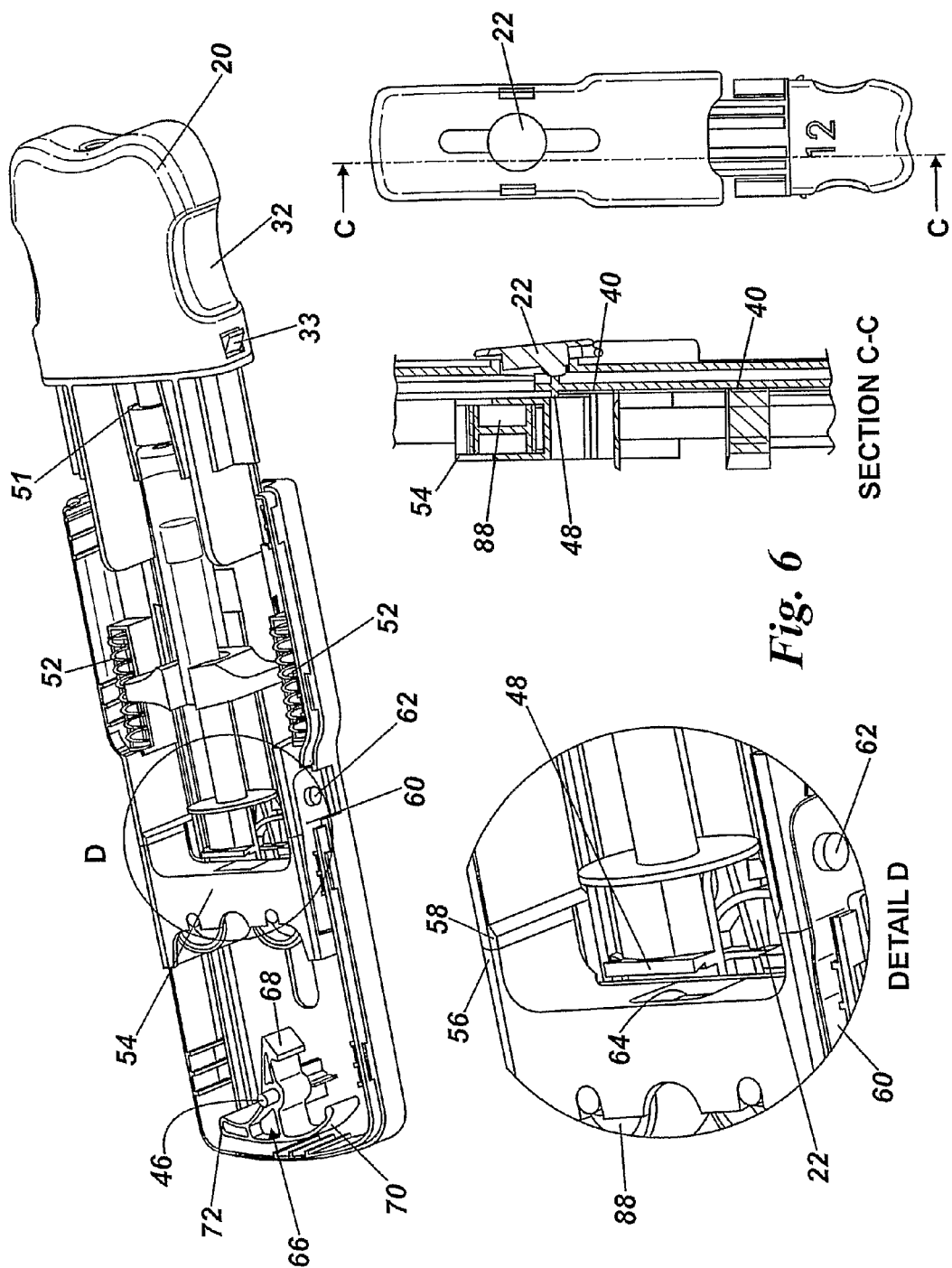

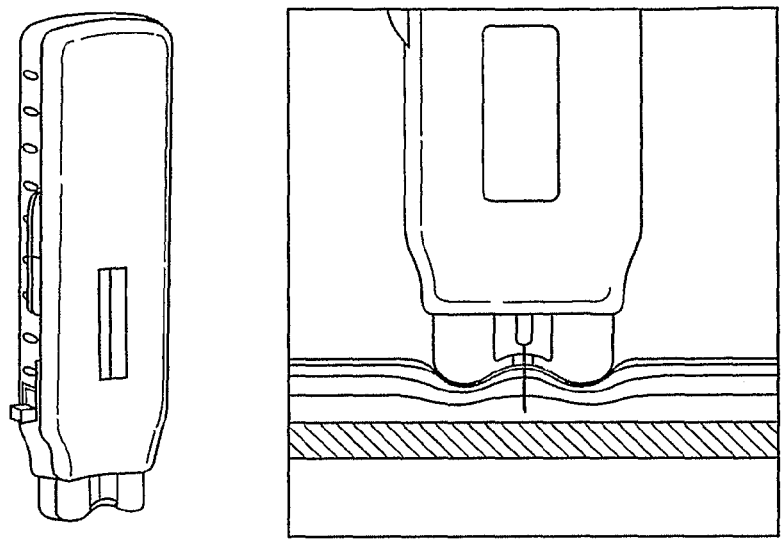
*Fig. 9*
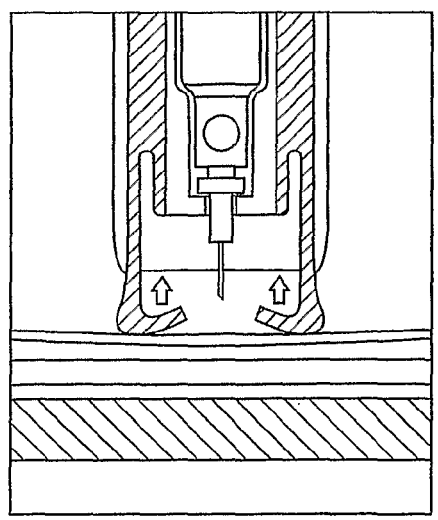 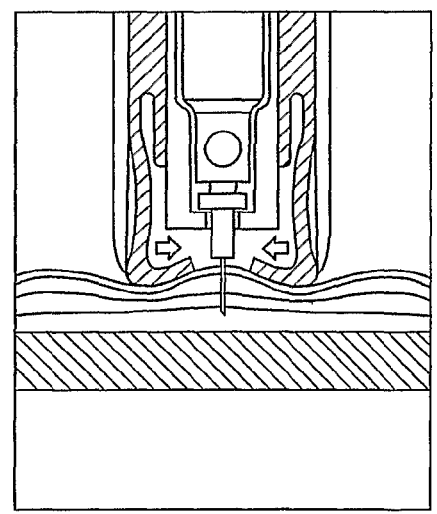
*Fig. 10(a)*        *Fig. 10(b)*

AUTOINJECTION DEVICES

BACKGROUND OF THE INVENTION

This invention relates to autoinjection devices and, in particular but not exclusively, to such devices intended for multiple use.

DESCRIPTION OF THE RELATED ART

Although single use autoinjection devices are common there are many instances where the autoinjection device is designed for reuse by the user or clinician and this is becoming more frequent due to environmental awareness. Where an autoinjection device is to be reused, it is important that the loading, priming, firing and unloading of the syringe is achieved simply and consistently by a wide range of potential users and also that there are safeguards against inadvertent operation.

SUMMARY OF THE INVENTION

According to one aspect of this invention there is provided an autoinjection device comprising:

a housing including a main body portion and a front body portion moveable longitudinally between a closed position and an open position allowing access to enable in use a syringe to be loaded into said housing, the syringe having a body, a plunger and a needle at a forward end of the body;

a drive member and a drive bias means disposed in said housing, the drive member being moveable against said drive bias means to a primed position and operable in use when released from said primed position to urge the syringe forwardly to an injection position, and to expel a dose therefrom; and trigger means for releasably retaining said drive member in its primed position, the device being operable to move said drive member to its primed position as the main body and the front housing portion are moved to their closed position.

In this way preferred arrangements of the device may be opened to insert a syringe and then closed to prime the drive mechanism.

To provide a safety feature, at least one of said front housing portion and said drive member is preferably moveable between an inactive configuration, in which closing movement of the front housing portion does not cause engagement with said drive member, and an active configuration, in which closing movement of said front housing portion applies directly or indirectly a rearward force to said drive member to move it to said primed position.

Thus the front housing portion may include a drive face adapted to be moved to cooperate with a drive face on the drive member.

An externally operable actuating member may be disposed on the main body portion and actuable to urge the drive faces into lateral engagement against a bias.

Conveniently, said front housing portion is operable to apply directly or indirectly a force to release said trigger means on movement of the front housing portion rearwardly from said closed position.

Again, for safety, at least one of said front housing portion and said trigger means may be changeable between an inactive configuration in which rearward movement of said front housing to engage said trigger means is prevented, and an active configuration, wherein, on rearward movement from said closed position, said front housing portion releases said trigger means.

An externally operable actuating member may be disposed on the main body portion and operable to switch the front housing portion and the trigger means to their active configuration.

A dual function actuating member may be provided for activating the priming stroke and for freeing the front housing portion for rearward motion to release the trigger means.

This safety feature may be provided by providing releasable safety latch means for preventing rearward movement of said front housing portion to release said trigger means until after said safety latch has been released.

Still further, to ensure that the needle is shrouded after an injection a lock out latch means may be provided for latching the forward housing portion against retracting means when it returns to a forward position on completion of an injection.

Both latching functions may be performed by a common releasable latching means. Indeed, in a particularly preferred arrangement a common actuating member and latching means may be provided.

To facilitate the injection, the housing may have an associated injection site contacting element having two lobes spaced to either side of the longitudinal axis of the needle and adapted in use, when the contact element is pressed against the user's flesh, to compress the flesh at spaced locations to either side of the injection axis and thereby to cause a bulge at the injection site.

Preferably said injection site contact element has only two lobes, and the contact element has a profile comprising a central concave region with two convex regions to either side thereof to define said lobes. In one arrangement said lobes are adapted to move towards each other as pressure is applied to said device, thereby to exert a pinching action to enhance said bulging effect.

In another aspect, this invention provides an autoinjection device comprising:

a housing having a main body portion, containing a drive mechanism, and a front body portion moveable longitudinally between a closed position and an open position allowing access to enable a syringe to be loaded therein for an autoinjection cycle, wherein closing of said housing is operable to energise the drive mechanism for the autoinjection cycle, and rearward movement of said front body portion beyond the closed position releases said drive mechanism.

The device advantageously includes an externally operable actuating member, operarable to affect at least one of the following functions:

to engage and/or disengage a load path between the forward body portion and a prime mover in the drive mechanism, to engage and/or disengage a load path between the forward body portion and a trigger for the drive mechanism, to prevent and/or allow rearward movement of the forward body portion prior to release of said trigger, to prevent and/or allow rearward movement of the forward drive portion from a shrouding position after completion of said injection operation.

In yet a further aspect, this invention provides an injection device comprising:

a housing including a main body portion and a front body portion relatively moveable longitudinally;

the housing being openable to provide access to allow a syringe to be loaded into the housing in use, the syringe having a body, a plunger and a needle at its forward end;

a drive member disposed within the housing and moveable against a drive spring bias to a primed position and operable in use when released from said primed position to urge the syringe forwardly within the housing to an injection position in which the syringe needle projects from the front end of the housing and to expel a dose therefrom;

a trigger for latching said drive member in its primed position;

said front body portion further being moveable against a housing spring bias rearwardly from a closed position to a fire position in which it unlatches said firing latch to free said drive member for forward movement under the influence of said drive spring bias;

wherein as said housing is moved away from the injection site following an injection, said housing spring bias urges said front body portion forwardly back towards its closed position to shroud said needle;

a releasable safety latch preventing rearward movement of said front body portion from its closed position until release of the safety latch, and a latch for latching said forward body portion in its extended, shrouding, position.

Preferably said front body portion is movable longitudinally relative to said main body portion from said closed position to an open position providing access for said syringe. The front housing portion may include a drive face adapted to be moved to cooperate with the drive member to move the drive member to its primed position as the housing is moved from its open position to its closed position. An actuating member may be disposed on the main body portion for urging the drive face on the front body portion laterally into engagement with the drive member.

The said actuating member may also be operable to unlatch said safety latch whereby, at different phases of operation of the device, said actuating member is operable to urge said drive face on the forward drive portion into engagement with the drive member to release said forward body portion to allow it to move from said closed position to its firing position, and to lock out the forward drive portion on completion of an injection.

Preferably said front body portion includes a unitary element slideably mounted for telescopic movement relating to said main body portion. Said unitary front body portion may include a shroud region for said needle, a latch surface for cooperating with said releasable safety latch, and a drive face resiliently moveable into engagement with said drive member. The drive member is preferably longitudinally slideably mounted within said housing, with said drive spring bias comprising at least one spring. The drive spring bias preferably comprises two co-acting springs, which advantageously each comprise a constant force spring.

Conveniently, said housing includes at its forward end thereof an interchangeable nose element, the contact nose element being interchangeable to adjust the penetration depth of the injection.

In another aspect, this invention provides an injection device comprising:

a housing;

said housing being adapted in use to receive a syringe having needle at its forward end;

a drive member moveable against a spring bias to a primed position and releasable in use to urge said syringe to a forward position and to expel a dose;

a trigger for latching said drive member in its primed position;

an actuating member having a shroud portion at a forward region thereof and moveable between a forward position and a rearward position;

actuating member bias means biasing said actuating member towards its forward position;

said actuating member being adapted in use when moved to its rearward position to release said firing latch to free said drive member for movement;

the actuating member thereafter being movable forward under the influence of said actuating member bias means to return to its forward position with said shrouding region in use shrouding the needle when the needle is at its forward position, and releasable latch means for locking said shroud member against movement from its forward position.

In yet another aspect this invention provides an injection device comprising a needle through which a dose is delivered and, adjacent said needle, a skin contact surface, said skin contacting surface comprising two lobes spaced to either side of the longitudinal axis of the needle and, adapted in use, when the contact element is pressed against the skin, to compress the flesh space locations to cause a bulge at the injection site.

In still a further aspect, this invention provides an auto-injection device comprising a housing for receiving a syringe, and having a drive mechanism for releasable to urge the syringe forwardly to an injection position and to expel a dose therefrom, said drive mechanism comprising a drive member mounted for sliding movement within said housing and acted upon by two constant force spring arrangements.

Whilst the invention has been described above, it extends to any inventive combination or sub-combination of the features set out above, or in the following description or claims.

BRIEF DESCRIPTION OF THE DRAWING FIGURES

The invention may be performed in various ways, and embodiment thereof will now be described by way of example only, reference being made to the accompanying drawings in which.

Figures 5A, 5B:
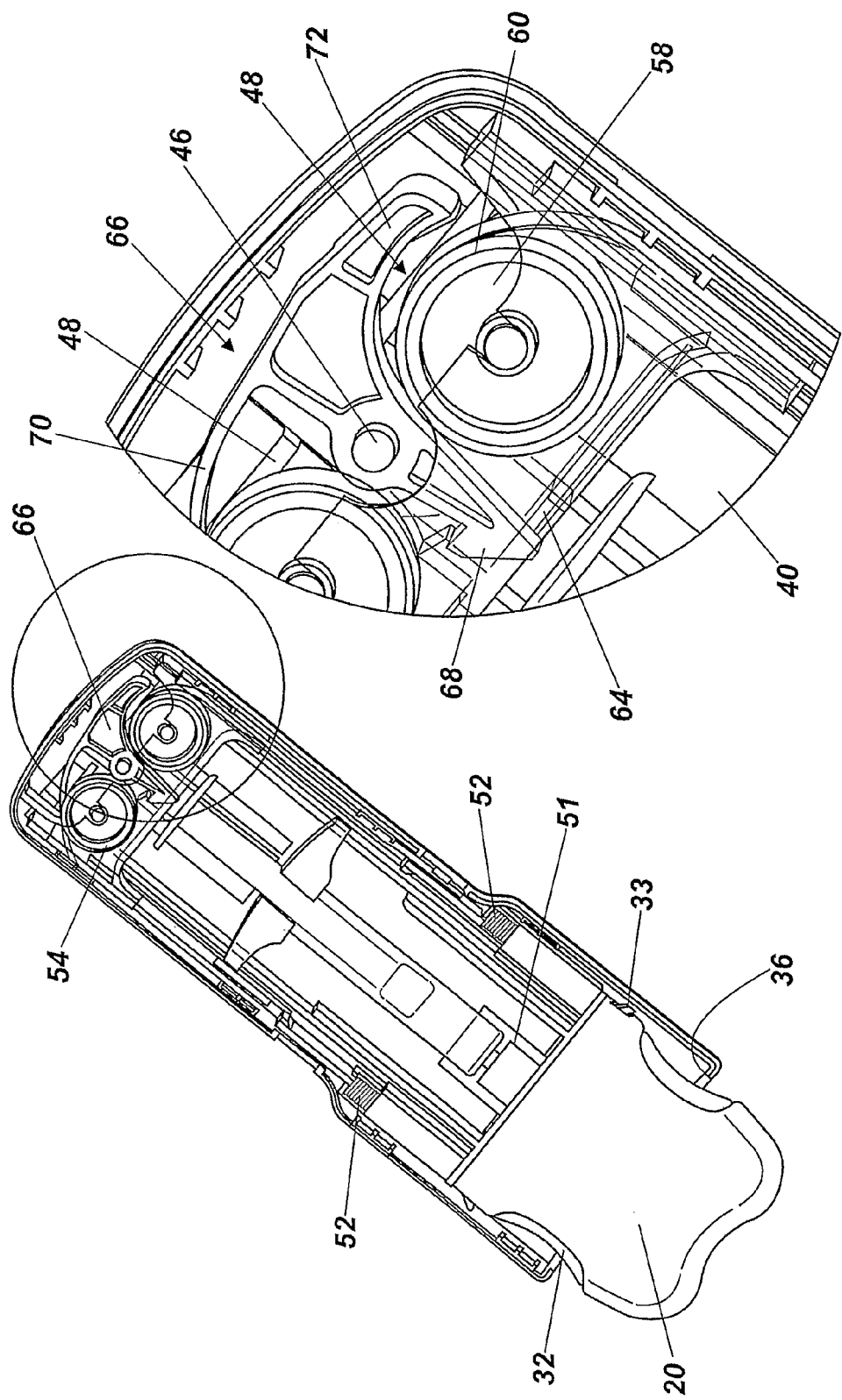
Figure 7:
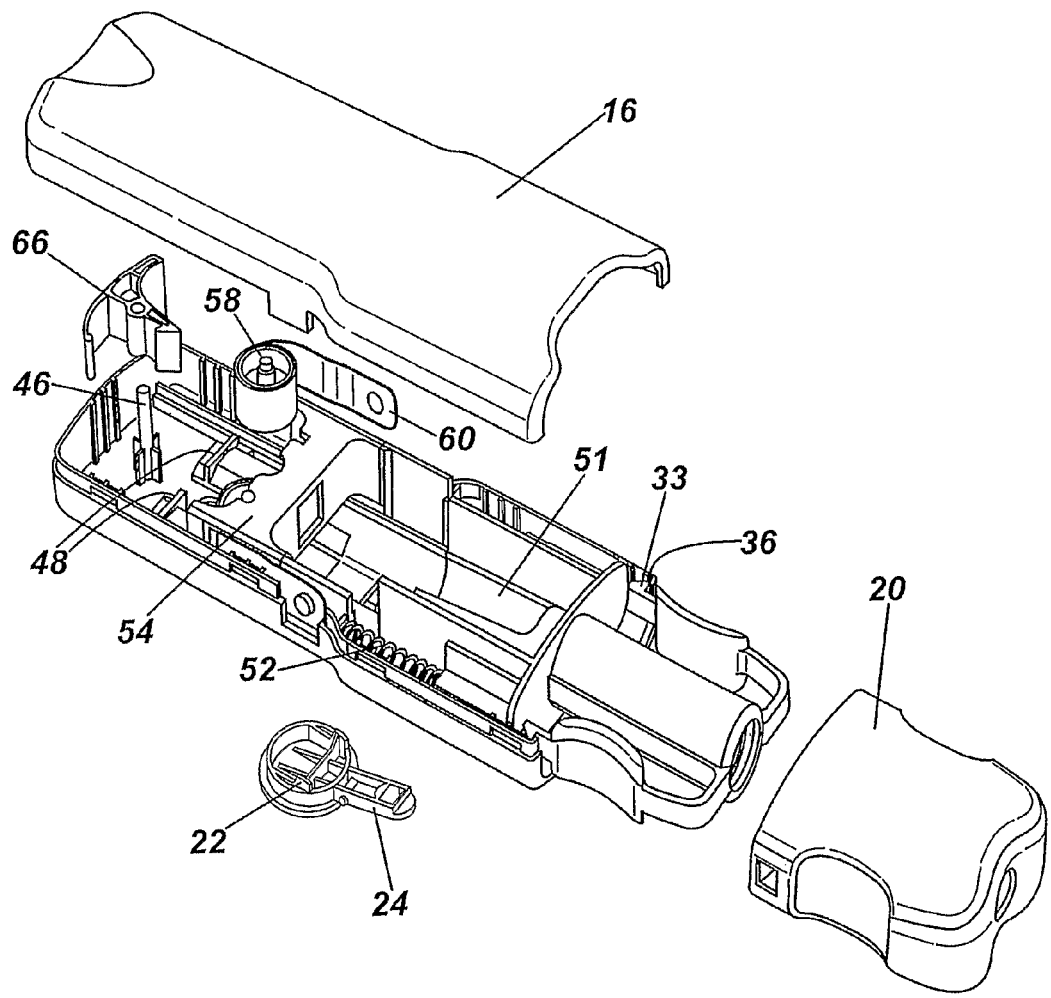
Figure 8:
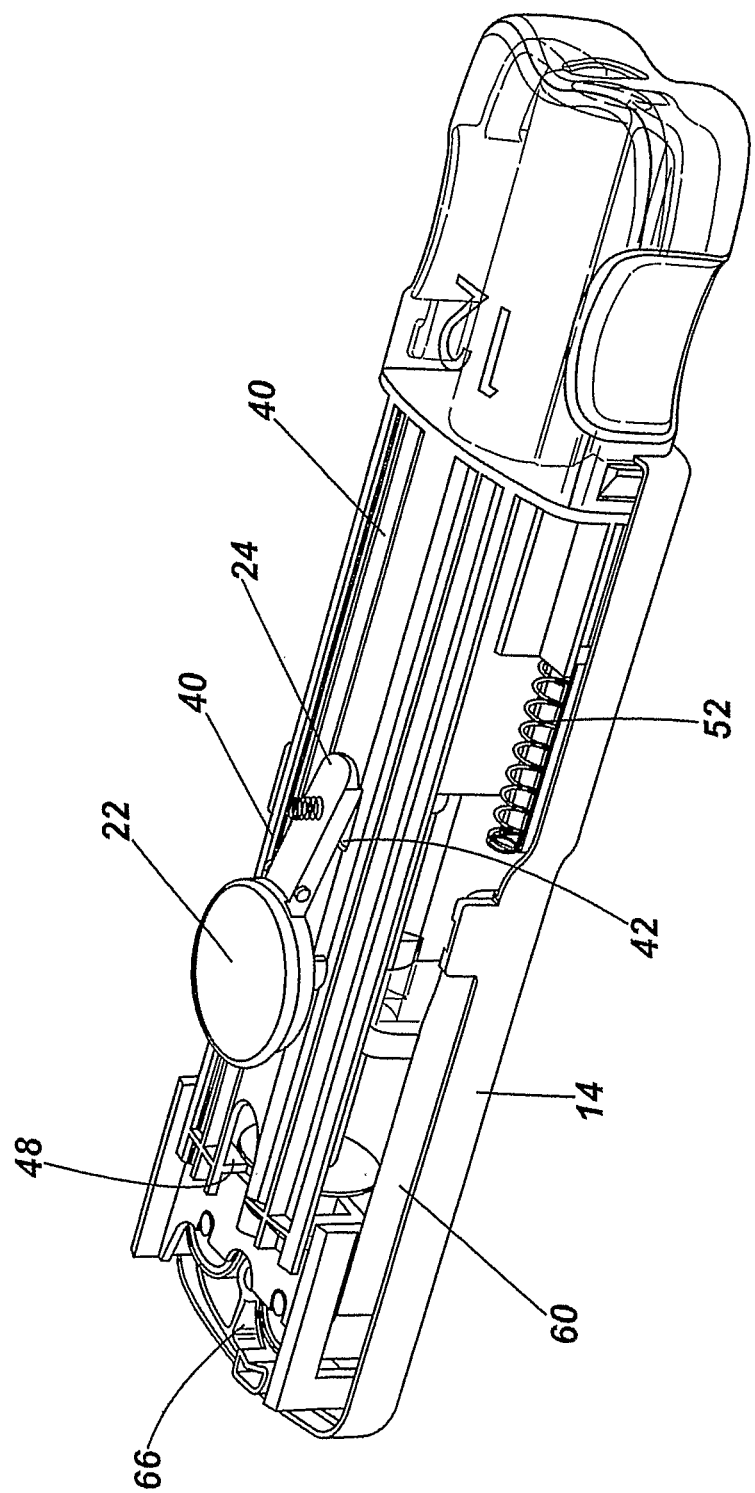

FIGS. 5(a) and (b) are a view of the injection device when closed in a primed condition with the top cover removed, and a detail showing the latch mechanism respectively;

FIG. 6 are respective views of the injection device at the start of a priming action with the multi-function button depressed and urging the rear part of the drawer into engagement with the drive member, a detail on said view, and a detailed section view respectively;

FIG. 7 is a part-assembled view of the injection device;

FIG. 8 is a view from the underside of the injection device with the lower body removed showing interaction of the button and the drawer;

FIG. 9 is a schematic view showing the effect of the wide footprint of the nose of the injection device when applied to a user's skin;

FIGS. 10(a) and (b) are schematic section views of a modified form of nose designed actively to exert a pinching action on the injection site, and FIGS. 11(a) to (f) illustrate successive stages during operation of the device of FIGS. 1 to 8.

DETAILED DESCRIPTION OF THE INVENTION

Referring initially to FIGS. 1 to 4 the reusable auto injector of the present invention is designed to have a slim compact rectangular form closed of length not much greater than that of the syringe and needle cap.

Figure 3:
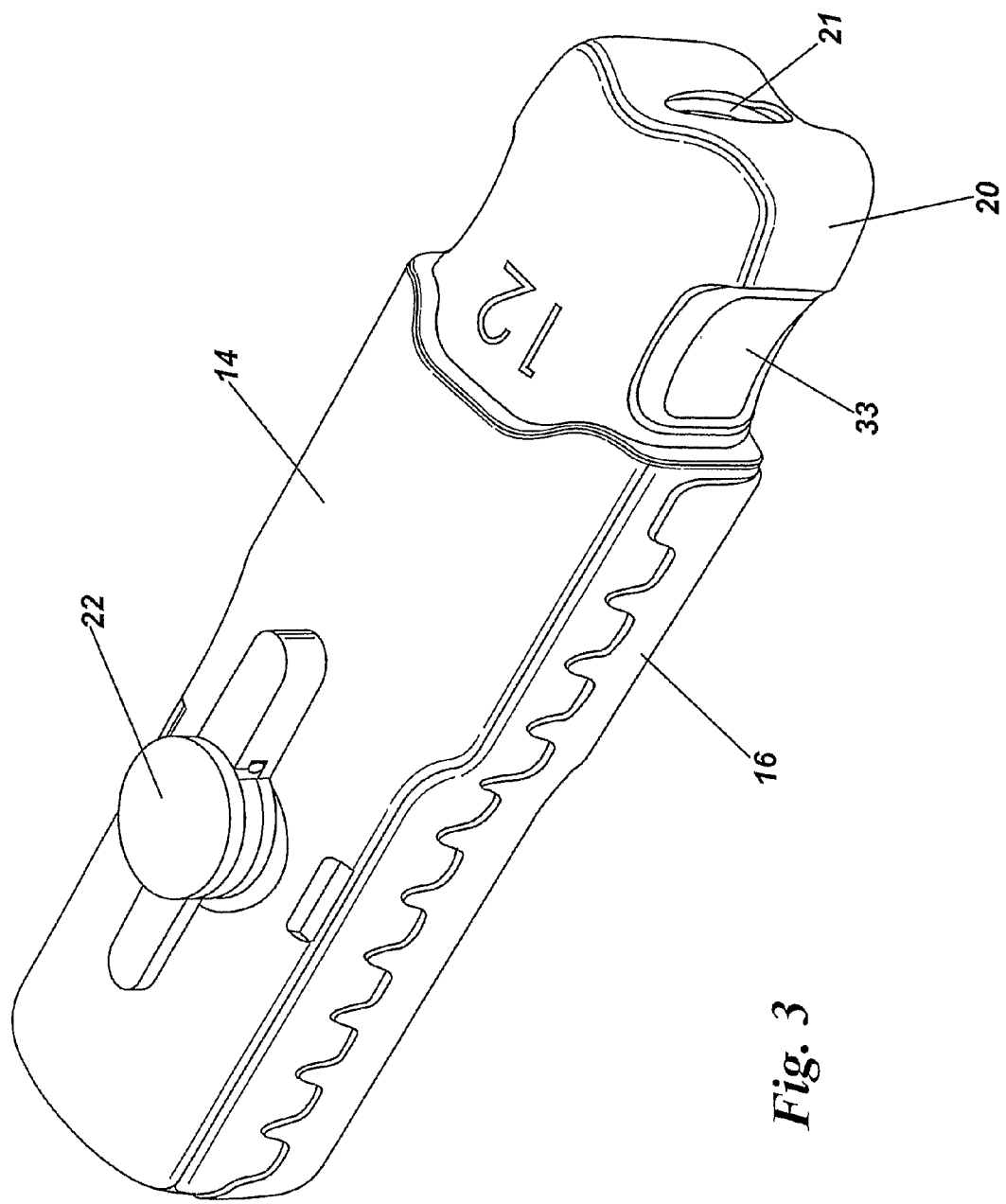
FIG. 3 is a bottom perspective view when closed.

The auto injector indicated generally at 10 comprises a main body portion 12 made up of a lower casing part 14 and an upper casing part 16 to define a body of generally rectangular form open at one end to receive slideably a drawer or front body portion 18. On the forward end of the drawer 18 is a nose piece 20. The nose piece may be interchangeable so as to provide a number of options for the injection depth. Typically injection depth may be 8, 10 and 12 mm penetration depth. On the underside of the housing, as seen in FIGS. 3 and 4, there is a multi-function button 22 having an integral forwardly extending arm 24 and being mounted for rocking movement in the lower casing part 14.

Figure 4:
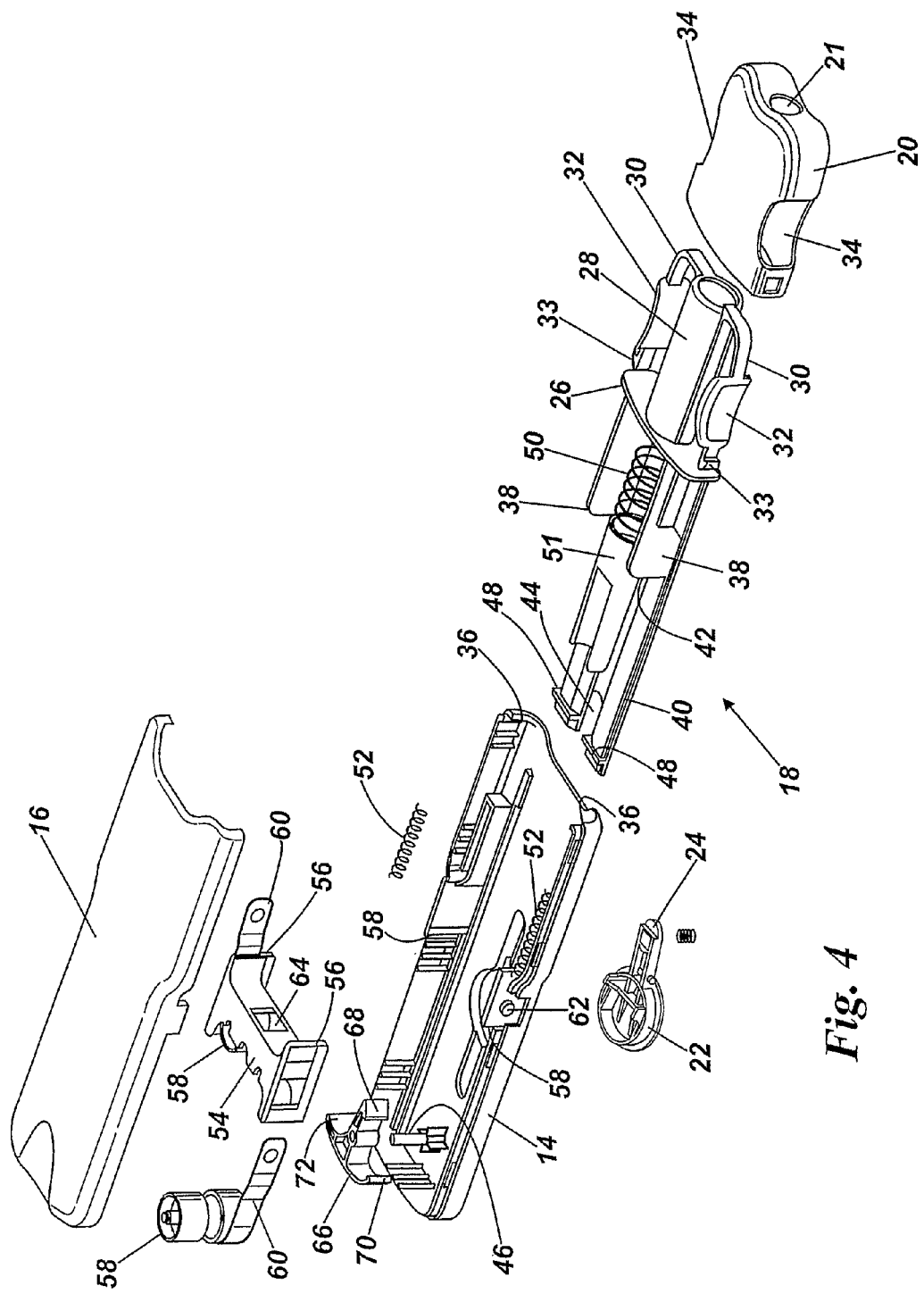
FIG. 4 is an exploded view of the injection device.

Turning more specifically to FIG. 4, the drawer 18 comprises a main transverse web 26 from which extends forwardly a cylindrical tubular portion 28. From the front end of the tubular portion 28 extends first laterally then rearwardly two spring arms 30 with finger pads 32 that align with apertures 34 in the nose piece 20. At their rearward ends, the spring arms 30 terminate in barbed portions 33 which latch behind abutment surfaces inside an inner lip 36 of the main body portion 12 releasably to latch the drawer in its closed position. Extending rearwardly from the main web 26 are two side webs 38 between which there is a floor 40 extending well to the rear of the webs 38. The drawer in this embodiment is formed integrally from a single plastic moulding. In the floor, just to the rear of the side webs 38 is a latch aperture 42 that cooperates with the arm 24 of the multi-function button 22 in a manner to be described below.

At the rear end the floor 40 has a cut out to accommodate a pivot post 46 upstanding from the lower casing 14. Upstanding from the spaced edges of the floor 40 to either side of the cut out portion 44 are upwardly projecting ribs 48. Slideably received in the inside of the tubular portion 28 of the drawer 18 is a compression spring 50 and the forward end of a part cylindrical syringe carriage 51 cut away to allow a syringe to be introduced as to be described below. The drawer 18 is urged forwardly by twin drawer springs 52 which are received inside pockets on the lower body casing and act against the main web 26 of the drawer to push it forwardly so that the barbs 33 are normally in engagement with the lip 36 on the housing.

Slideably mounted in the lower casing part 14 is a drive member 54, the forward extent of movement of the drive member 54 being limited by horns 56 on the drive member abutting internal ribs 58 on the lower casing 14. The drive member is urged forwardly relative to the lower casing by a pair of constant spring arrangements each comprising a drum 58 rotatably mounted on the drive member around which is wrapped a constant force spring 60 whose apertured free end is anchored to the lower casing 14 by a peg 62. By using twin constant force spring arrangements the loading on the drive member is symmetric and also the size of the springs required can be reduced thereby giving a flatter, more compact arrangement. The lower casing 14 may be provided with 'end of dose' apertures through which part of the drive member 54 is visible only when it is in its fully forward position with the horns 56 adjacent the abutments 58. The drive member 54 has a latching aperture 64 which cooperates with a T-shaped latch 66 which is mounted for pivoting movement on the pivot post 48. At the base of the T of the latch 66 is a barbed latch surface which engages the latch aperture 64 releasably to retain the drive member in a primed position against the bias afforded by the constant force springs 60. One of the cross limbs of the latch 66 is anchored in the lower casing 14 and acts as a resilient bias 70 urging the barb 68 to its latching position. The other cross piece of the latch comprises an abutment surface 72 that is engageable by one of the ribs 48 on the rear end of the drawer when suitably deflected upwards by the multi-function button 22.

Figure 1:
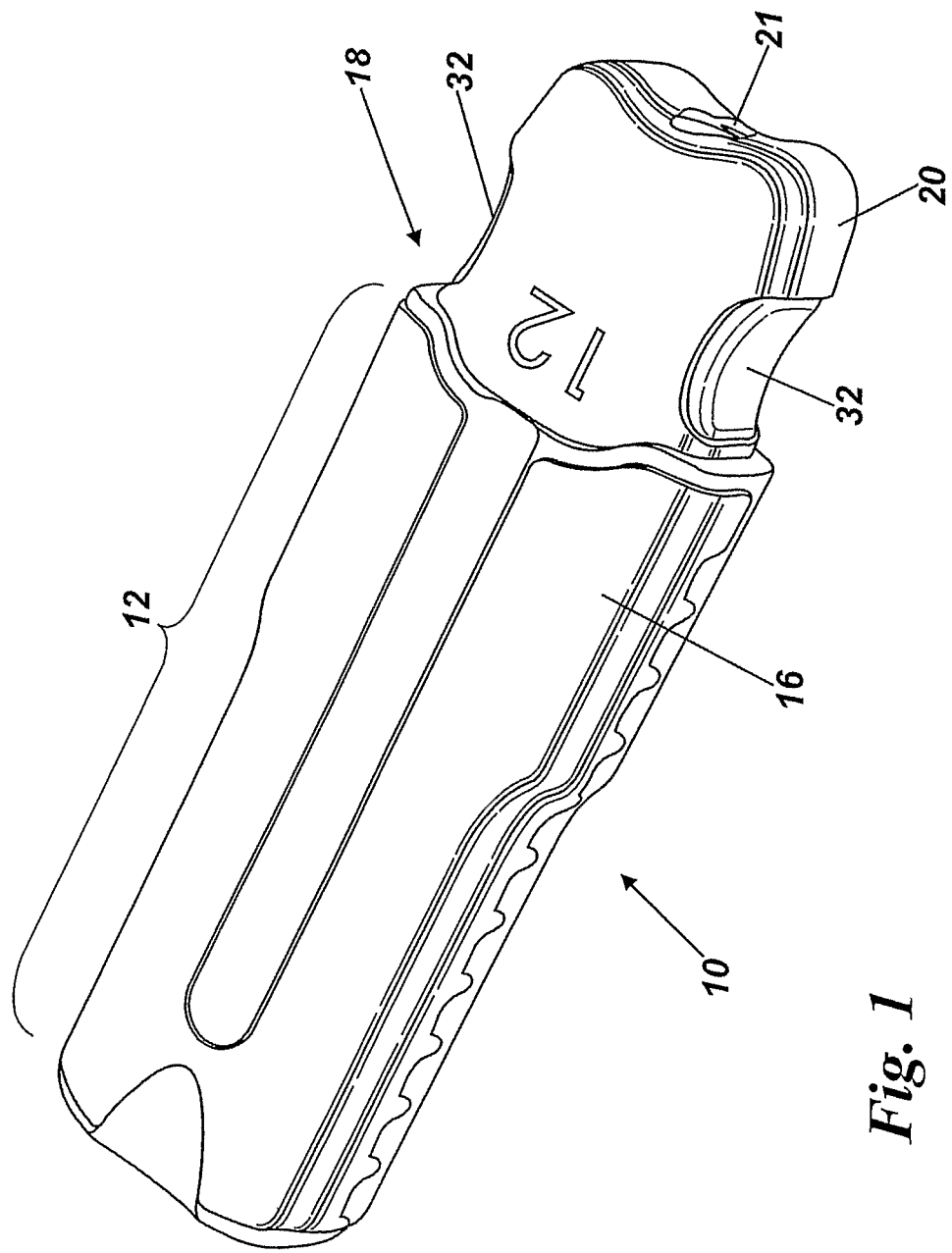
FIG. 1 is a top perspective view of the injection device when closed.
Figure 2:
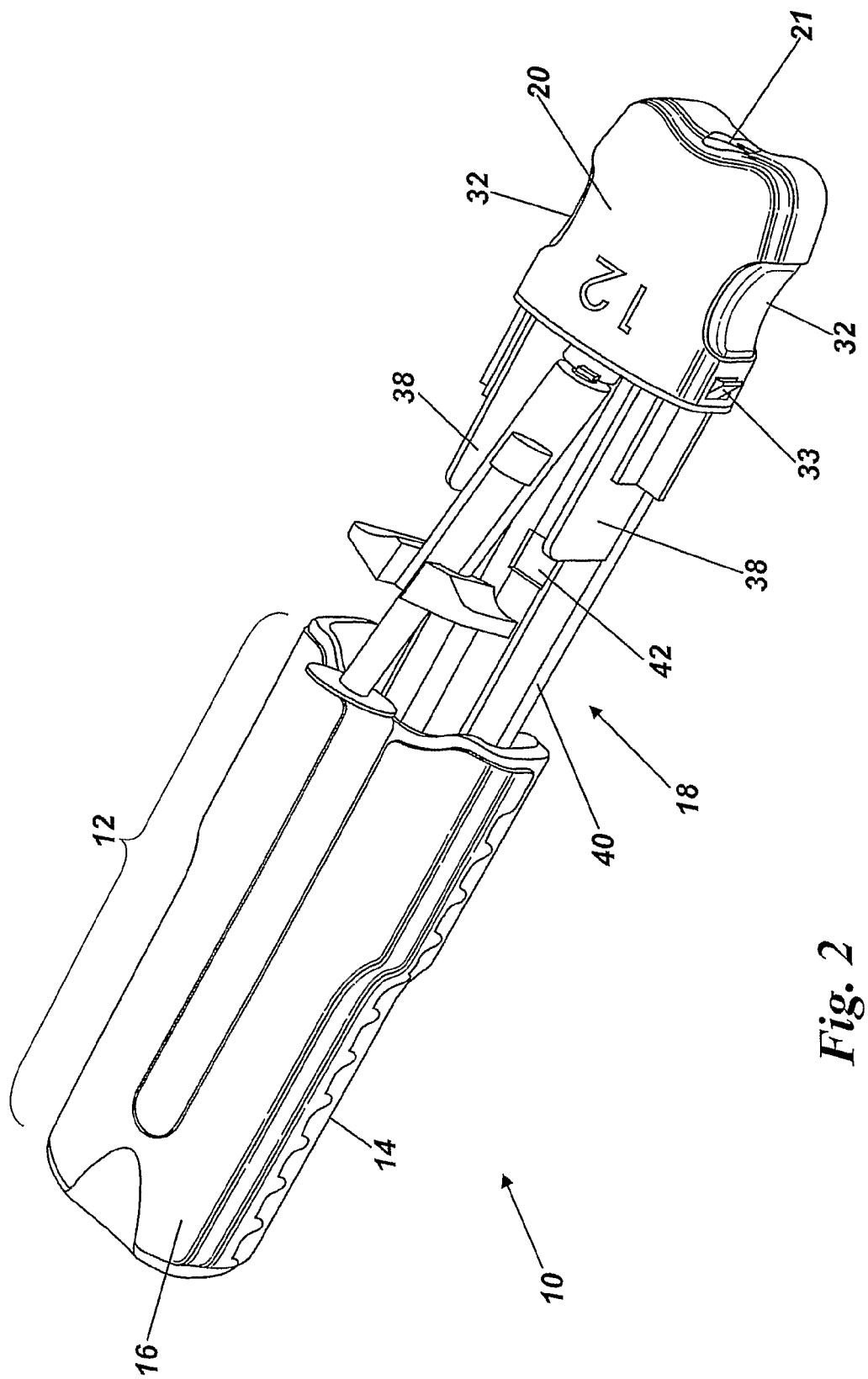
FIG. 2 is a top perspective view of the injection device when open for insertion of a syringe.

Referring now to FIGS. 11(a) to (f) operation of the device will now be described. From a closed position as shown in FIGS. 1 and 3, the device is moved to an open position by squeezing the finger pads 32 thus pulling the barbs 33 out of engagement with the lip 36 and pulling the drawer forwardly to allow access to the syringe carriage 51 (FIG. 11(a)). A syringe may then be inserted into the carriage 51 and dropped into place (FIG. 11(b)). In doing this the needle cap is trapped by the keyhole shaped opening 21 in the nose piece 20, thus holding the syringe forwardly in the drawer against the bias of the carriage spring 50 (FIG. 11(c)). When the needle cap is removed, the syringe springs back to become captive inside the device thereby shrouding the needle.

In order to prime the device, the multi-function button 22 is pressed which in turn presses the floor 40 of the drawer away from the opposed surface of the lower casing 14 so that the ribs 48 are aligned with a transverse surface of the drive member 54. At the same time the device is pushed down on a flat surface (FIG. 11(d)) to push the drawer 18 back into the main body and at the same time pushing the drive member 54 rearwardly until it is latched in the primed position by means of the latch 66. As the drawer returns to its closed position, the barbs 33 move past the inward lip 36 and prevent forward movement of the drawer. At the same time the arm 24 on the multi-function button 22 latches in latch aperture 42 in the floor 40 of the drawer 18, to prevent rearward movement. It will be noted that the device cannot be primed without the compound action of both pressing the multi-function button 22 and pushing the nose against a firm surface to move the drive member 54 rearwardly to latch it.

Figure 11A:
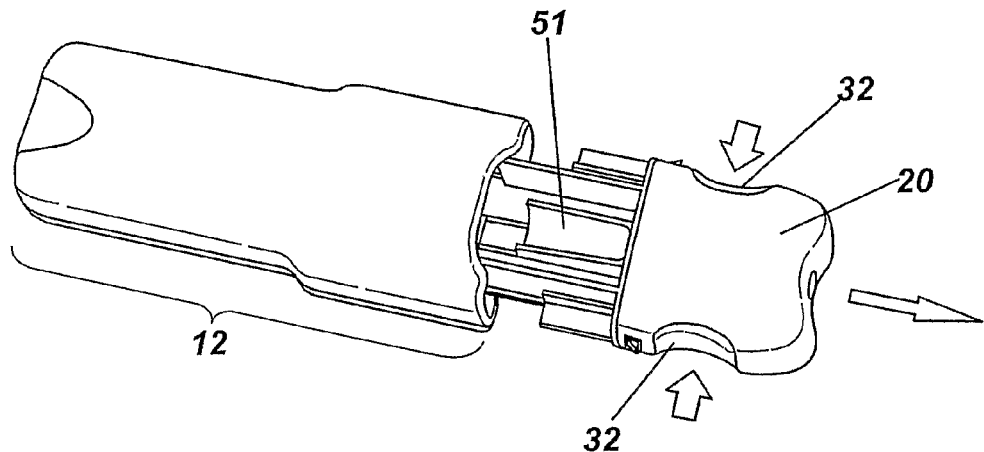
Figure 11B:
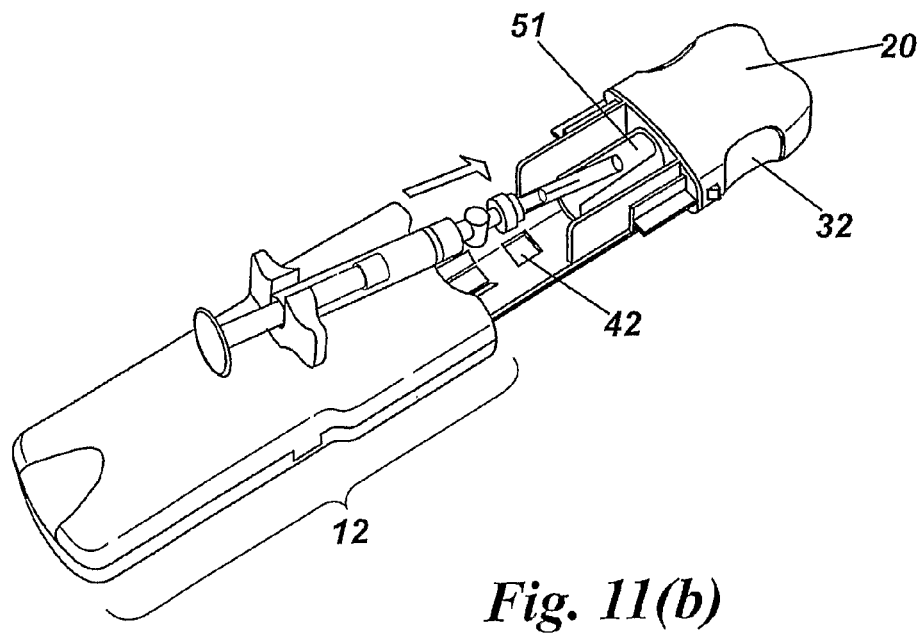
Figure 11C:
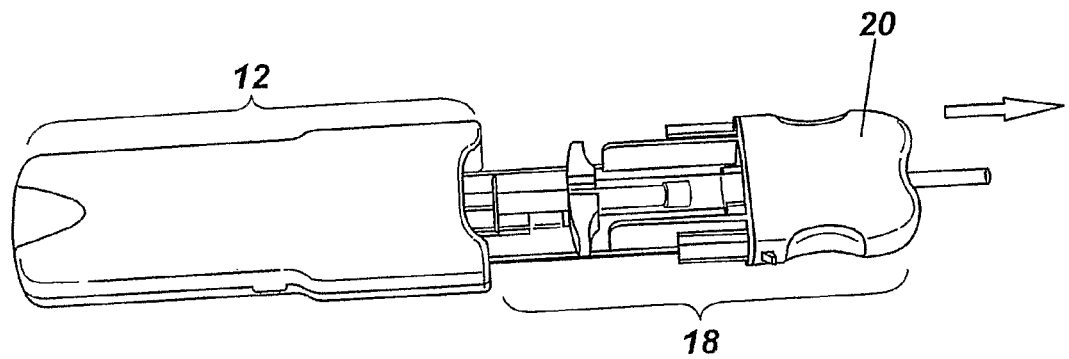
Figure 11D:
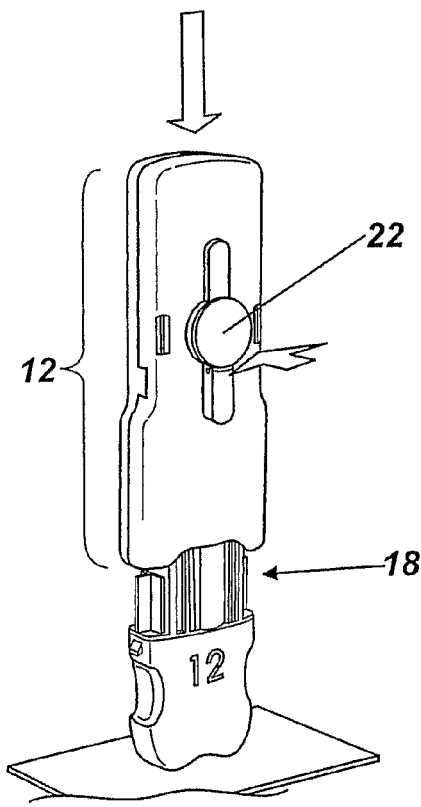
Figure 11E:
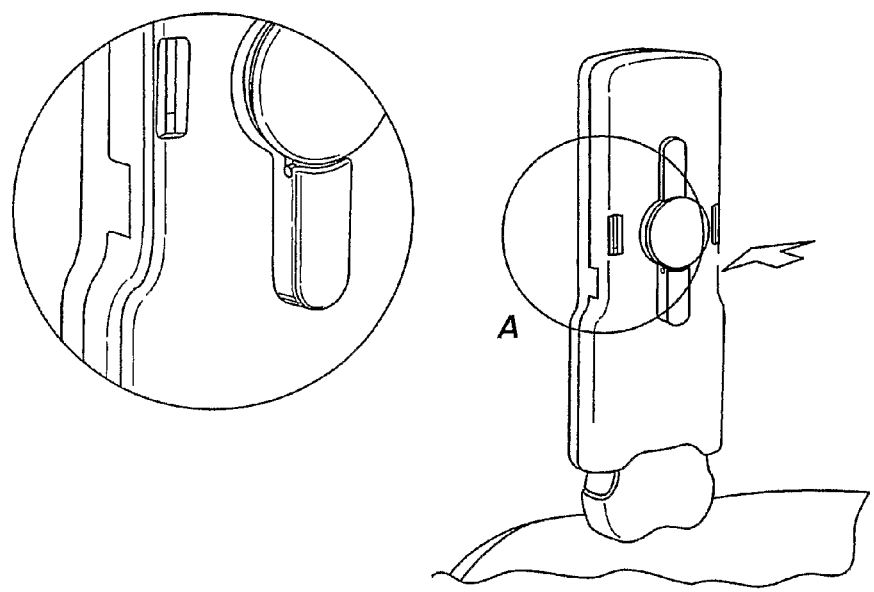
Figure 11F:
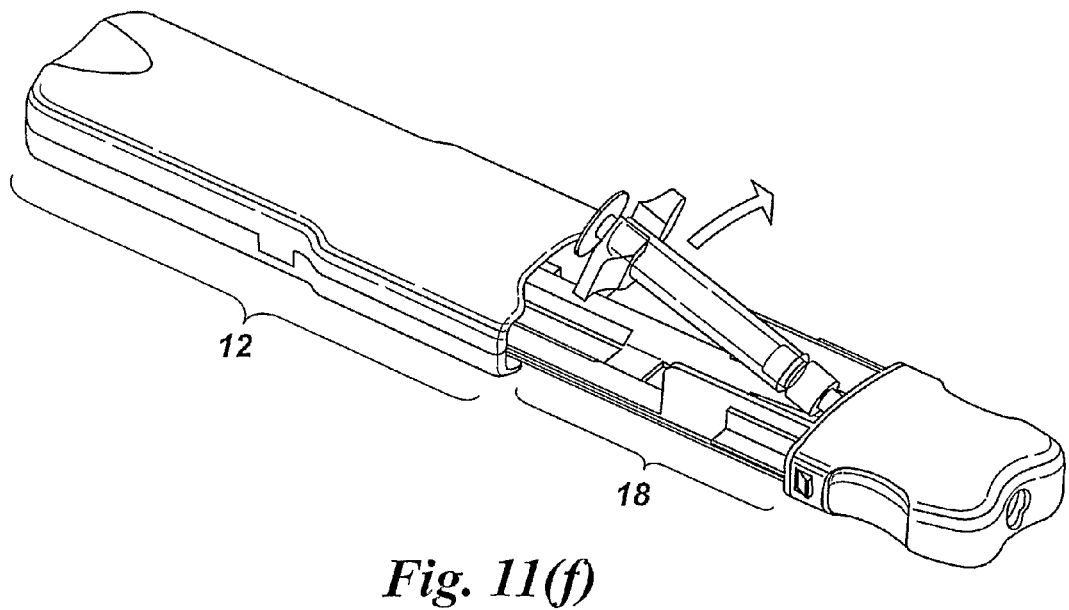

In order to fire the device it is offered up to the injection site (FIG. 11(e)) and the multi-function button 22 depressed to exert two functions; firstly, it lifts the arm 24 out of the latching recess 42 so allowing the drawer to move back into the housing towards the firing position and secondly, it again lifts the floor 40 of the drawer away from the internal surface of the lower casing so that the right hand rear rib 48 as viewed in FIG. 4 is aligned with the abutment surface on the trigger and so as the drawer reaches its rearmost position, it pivots the latch 66 thus releasing the drive member 54. The drive member moves under the influence of the constant force springs firstly to drive the syringe forwardly and thereafter to expel a dose as the plunger moves relative to the syringe. It is to be noted that, unless the button 22 is pressed to lift the floor of the drawer 40 upwardly, the rib 48 will simply pass underneath the abutment 72 and thus not trip the latch. This embodiment therefore requires that, for an injection to occur, there must be sustained pressure applied to the multi-function button 22 not only to release the drawer for rearward movement but also to ensure that the rib 48 engages the release abutment.

When the user releases pressure from the main body portion on completion of an injection, the drawer 18 moves back forwardly to its initial position under the influence of the drawer springs 52 and in so doing, shrouds the needle of the syringe. As it nears the rest position, the finger 24 again latches into the latch aperture 42 on the drawer thus effectively locking the drawer against retraction movement and ensuring that the needle remains shrouded.

Finally, to unload the device, the finger pads 32 are pressed and the drawer moved forwardly to allow access to the syringe which is removed.

Referring to FIGS. 9 and 10, the traditional method of administering a subcutaneous injection with a syringe (without an auto injector) is to pinch the flesh skin at the injection site and to insert the needle at the centre of the pinched fold of skin. This creates depth in the subcutaneous layer ensuring the needle does not enter the muscle layer below, it also relieves pressure under the skin thereby making it easier to inject the drug. With some known types of auto injector, the surface area of the device contacting the skin is typically relatively small and immediately adjacent the injection axis. Such devices can therefore have the effect of actually thinning the subcutaneous layer due to the pressure and increasing pressure under the skin, especially if the footprint is small. However in the present embodiments it will be noted that the nose 20 has a rounded 'w' profile where it contacts the injection site, defining two lobes 72 to either side of the injection axis. Applying pressure to two spaced locations to either side of the injection axis provides an effect similar to the pinching action commonly used when injecting into the subcutaneous layer.

It will be appreciated that this contact surface may be used on a wide variety of different devices beyond the embodiments described herein.

FIGS. 10 (*a*) and (*b*) describe a variation of this technique where the lobes of the injection contact surface instead of being static are defined on the ends of flexible arms which are configured such that as pressure is applied to the arms, the contact surfaces tend to move together thus enhancing the pinch effect. Thus in these Figures, the forward end of the housing is provided with two inwardly facing L-shaped members with rounded contact surfaces designed to roll inwards as pressure is applied.

The invention claimed is:

1. An autoinjection device comprising:
 a housing for loading and firing a syringe, the syringe having a body, a plunger, and a needle at a forward end of the body, the housing including
  i) a main body portion having an open front end, and
  ii) a front body portion having a drawer portion and terminating with a nose piece, the front body portion being disposed in the open front end of the main body portion as a drawer slideably moveable longitudinally with respect to within the main body portion between
   a) a closed position in which the drawer portion is disposed within the main body portion and a forward portion of the nose piece extends forwardly beyond the open front end of the main body and, in use, in the closed position the syringe has been loaded into the housing, and
   b) an open position in which the syringe has not been loaded into the housing, and where a rear end portion of the drawer portion is disposed within the main body portion, and the nose piece and a forward portion of the drawer portion extend forwardly beyond the open front end of the main body,
  wherein the front body portion being in the opening position allows access to the drawer portion of the front body portion to enable, in use, the syringe to be loaded into the front body portion so that the needle is shrouded by the nose piece of the front body portion;
 a drive member and a drive bias arrangement disposed in said housing, the drive member having a primed position and being moveable longitudinally within the main body portion, the drive member being a) moveable against said drive bias arrangement to the primed position and b) operable in use when released from the primed position to urge the syringe forwardly to an injection position, and to expel a dose therefrom, wherein movement of the front body portion from the open position into the closed position moves the drive member rearwardly within the main body portion and against said drive bias arrangement into the primed position; and
 a trigger for releasably retaining said drive member in the primed position.

2. An autoinjection device according to claim 1, wherein at least one of said front body portion and said drive member is moveable between:
  i) an inactive configuration in which closing movement of the front body portion does not cause engagement with said drive member, and
  ii) an active configuration in which closing movement of said front body portion applies directly or indirectly a rearward force to said drive member to move said drive member to said primed position.

3. An autoinjection device according to claim 2, wherein the front body portion includes a drive face adapted to be moved to cooperate with a drive face on the drive member.

4. An autoinjection device according to claim 3, further comprising an externally operable actuating member disposed on the main body portion and actuable to urge the drive faces into lateral engagement against a bias.

5. An autoinjection device according to claim 4, wherein the externally operable actuating member disposed on the main body portion is additionally operable to urge the front body portion and the trigger to their active configuration.

6. An autoinjection device according to claim 1, wherein said front body portion is operable to apply directly or indirectly a force to release said trigger on movement of the front body portion rearwardly from said closed position.

7. An autoinjection device according to claim 6, wherein at least one of said front body portion and said trigger is moveable between:
  i) an inactive configuration in which rearward movement of said front body portion does not cause engagement with said trigger, and
  ii) an active configuration, wherein, on rearward movement from said closed position, said front body portion releases said trigger.

8. An autoinjection device according to claim 7, further comprising an externally operable actuating member disposed on the main body portion and operable to urge the front body portion and the trigger to the active configuration.

9. An autoinjection device according to claim 6, further comprising a releasable safety latch that prevents rearward movement of said front body portion to release said trigger until after said safety latch has been released, thereby preventing inadvertent firing.

10. An autoinjection device according to claim 9, wherein a common releasable safety latch means is provided for:
   i) preventing rearward movement of the front body portion prior to an injection to prevent inadvertent firing, and
   ii) preventing retraction movement of the front body portion after the injection in order to shroud the needle.

11. An autoinjection device according to claim 9, wherein, a common releasable latching is provided for preventing rearward movement of the front body portion prior to an injection to prevent inadvertent firing, and to prevent retraction movement of the front body portion after the injection to shroud the needle, and
   said trigger and said common releasable latch are defined by a common member.

12. An autoinjection device according to claim 6, further comprising a lock-out latch element that latches the front body portion against a retracting element when the front body portion returns to a forward position on completion of an injection.

13. An autoinjection device according to claim 1, wherein the nose piece has an associated injection site contact element having two lobes spaced to either side of the longitudinal axis of the needle, the two lobes being adapted in use, when the contact element is pressed against the user's flesh, to compress the flesh at spaced locations to either side of the injection axis and thereby to cause a bulge at the injection site.

14. An autoinjection device according to claim 13, wherein said injection site contact element has only two lobes.

15. An autoinjection device according to claim 14, in which the injection site contact element has a profile comprising a central concave region with two convex regions to either side of the central concave region to define said two lobes.

16. An autoinjection device according to claim 13, wherein said two lobes are adapted to move towards each other as pressure is applied to said injection device thereby to exert a pinching action to enhance said bulge at the injection site.

17. An autoinjection device according to claim 1, wherein,
   the front body portion is further moveable longitudinally within the main body portion from the closed position further into the main body portion to a firing position,
   with the front body portion in the firing position, a rear part of the forward portion of the nose piece is disposed within the main body portion and a forward part of the forward portion of the nose piece extends forwardly beyond the open front end of the main body portion, and
   the front body portion is moveable from the closed position into the firing position only upon operation of the trigger.

18. An autoinjection device according to claim 1, wherein said drive bias arrangement comprises two co-acting drive springs.

19. An autoinjection device according to claim 18, wherein said two co-acting drive springs each comprise a constant force spring.

20. An autoinjection device according to claim 1, wherein said housing includes at a forward end of the housing, an interchangeable contact nose element, the contact nose element being interchangeable to adjust a penetration depth of the injection.

21. An autoinjection device according to claim 1, wherein, the nose piece comprises a skin contacting surface, said skin contacting surface comprising two lobes spaced apart from each other on opposite sides of a longitudinal axis of the needle and, in use, when the autoinjection device is pressed against a patient's skin surface, said two lobes are adapted to compress locations on the patient's skin surface on either side of an injection axis to cause a bulge at an injection site.

22. An autoinjection device according to claim 21, wherein said two lobes are adapted to move towards each other as pressure is applied to said device, thereby to exert a pinching action to enhance said bulge at the injection site.

23. The autoinjection device according to claim 1, wherein,
   said drive member is mounted for sliding movement within said housing, and
   further comprising two constant force spring arrangements, wherein the two constant force spring arrangements act simultaneously upon the drive member in a common direction.

24. An autoinjection device comprising:
   a housing for loading and firing a syringe, the syringe having a body, a plunger, and a needle at a forward end of the body, the housing having
      i) a main body portion having an open front end, and
      ii) a front body portion having a drawer portion and terminating with a nose piece, the front body portion being disposed in the open front end of the main body portion as a drawer slideably moveable longitudinally within the main body portion between
         a) a closed position in which the drawer portion is disposed within the main body portion and a forward portion of the nose piece extends forwardly beyond the open front end of the main body and, in use, in the closed position the syringe has been loaded into the housing for an autoinjection cycle, and
         b) an open position in which the syringe has not been loaded into the housing, and where a rear end portion of the drawer portion is disposed within the main body portion, and the nose piece and a forward portion of the drawer portion extend forwardly beyond the open front end of the main body,
   wherein the front body portion being in the opening position allows access to the drawer portion of the front body portion to enable, in use, the syringe to be loaded into the front body portion so that the needle is shrouded by the nose piece of the front body portion;
   the main body portion containing a drive mechanism, the drive mechanism including a drive member and a drive bias arrangement disposed in said housing, the drive member having a primed position and being moveable longitudinally within the main body portion, the drive member being a) moveable against said drive bias arrangement to the primed position and b) operable in use when released from the primed position to urge the syringe forwardly to an injection position, and to expel a dose therefrom, and
   wherein the front body portion is configured such that movement of the front body portion to the closed position energises the drive mechanism for the autoinjection cycle, and b) rearward movement of the front body portion beyond the closed position releases said drive mechanism, wherein movement of the front body portion from the open position into the closed position moves the drive member rearwardly within the main body portion and against said drive bias arrangement into the primed position.

25. An autoinjection device according to claim 24, further comprising an externally operable actuating member, operable to affect at least one of the following functions:
   to engage and/or disengage a load path between the front body portion and a prime mover in the drive mechanism,
   to engage and/or disengage a load path between the front body portion and a trigger for the drive mechanism,
   to prevent and/or allow rearward movement of the front body portion prior to release of said trigger,
   to prevent and/or allow rearward movement of the front body portion from a shrouding position after completion of an injection.

26. An injection device comprising:
   a housing for loading and firing a syringe, the syringe having a body, a plunger, and a needle at a forward end of the body, the housing having
      i) a main body portion having an open front end, and
      ii) a front body portion having a drawer portion and terminating with a nose piece, the front body portion being disposed in the open front end of the main body portion as a drawer slideably moveable longitudinally within the main body portion between
         a) a closed position in which the drawer portion is disposed within the main body portion and a forward portion of the nose piece extends forwardly beyond the open front end of the main body and, in use, in the closed position the syringe has been loaded into the housing for an autoinjection cycle, and
         b) an open position in which the syringe has not been loaded into the housing, and where a rear end portion of the drawer portion is disposed within the main body portion, and the nose piece and a forward portion of the drawer portion extend forwardly beyond the open front end of the main body,
      wherein the front body portion being in the opening position allows access to the drawer portion of the front body portion to enable, in use, the syringe to be loaded into the front body portion so that the needle is shrouded;
   a drive member moveable against a spring bias to a primed position and releasable in use to urge said syringe to a forward position and to expel a dose;
   a trigger that latches said drive member in the primed position;
   an actuating member having a forward region comprised of a shroud portion, the actuating member being moveable between a forward position and a rearward position;
   an actuating member bias arrangement which is configured to bias said actuating member towards the forward position of the actuating member, said actuating member being adapted, in use when moved to the rearward position of the actuating member, to release said trigger to free said drive member for movement, the actuating member thereafter being movable forward under the influence of said actuating member bias arrangement to return to the forward position of the actuating member with the shroud portion, in use shrouding the needle when the needle is at a forward position of the needle; and
   a releasable latch for locking said shroud portion against movement from a forward position of the shroud portion.

* * * * *